United States Patent
Sabra (10) Patent No.: US 6,936,006 B2
(45) Date of Patent: Aug. 30, 2005

(54) ATRAUMATIC INSERTION OF A SUBCUTANEOUS DEVICE

(75) Inventor: Mads C. Sabra, Copenhagen N (DK)

(73) Assignee: Novo Nordisk, A/S, Bagsvaerd (DK)

( * ) Notice: Subject to any disclaimer, the term of this patent is extended or adjusted under 35 U.S.C. 154(b) by 70 days.

(21) Appl. No.: 10/393,194

(22) Filed: Mar. 19, 2003

(65) Prior Publication Data

US 2003/0225361 A1 Dec. 4, 2003

Related U.S. Application Data (60) Provisional application No. 60/366,675, filed on Mar. 22, 2002.

(30) Foreign Application Priority Data

Mar. 22, 2002 (DK) ........................ 2002 00442

(51) Int. Cl.[7] ................................. A61B 5/00
(52) U.S. Cl. .................... 600/300; 600/309; 604/57; 604/59; 604/500; 604/93.01
(58) Field of Search ................... 600/300, 309, 600/327, 332, 345, 373, 381, 386, 478, 486, 562, 576.581, 325, 573, 576, 581; 604/57, 59, 93.01, 500, 115, 264, 272–274, 158, 160, 161, 27, 36; 606/108, 129; 204/403.01

(56) References Cited

U.S. PATENT DOCUMENTS

| | | | | |
|---|---|---|---|---|
| 3,064,651 A | * | 11/1962 | Henderson | 604/274 |
| 3,224,436 A | * | 12/1965 | Le Massena | 600/361 |
| 4,799,495 A | * | 1/1989 | Hawkins et al. | 600/567 |
| 4,931,059 A | * | 6/1990 | Markham | 606/185 |
| 5,158,565 A | * | 10/1992 | Marcadis et al. | 606/185 |
| 5,299,571 A | * | 4/1994 | Mastrototaro | 600/347 |
| 5,360,416 A | | 11/1994 | Ausherman et al. | 604/272 |
| 5,390,671 A | | 2/1995 | Lord et al. | 128/635 |
| 5,391,950 A | | 2/1995 | Krawczak | 327/384 |
| 5,482,473 A | | 1/1996 | Lord et al. | 439/67 |
| 5,568,806 A | | 10/1996 | Cheney, II et al. | 128/635 |
| 5,586,553 A | * | 12/1996 | Halili et al. | 600/316 |
| 5,779,665 A | * | 7/1998 | Mastrototaro et al. | 604/506 |
| 5,800,389 A | | 9/1998 | Burney et al. | 604/158 |
| 5,853,391 A | | 12/1998 | Bell | 604/160 |
| 5,954,643 A | | 9/1999 | VanAntwerp et al. | 600/316 |
| 6,203,524 B1 | * | 3/2001 | Burney et al. | 604/93.01 |
| 6,484,045 B1 | * | 11/2002 | Holker et al. | 600/345 |

OTHER PUBLICATIONS

Adam Heller, Annual Review Biomed. Eng. vol 01, pp. 153–175, (1999).

* cited by examiner

*Primary Examiner*—Robert L. Nasser
*Assistant Examiner*—Patricia C Mallari
(74) *Attorney, Agent, or Firm*—Marc A. Began, Esq.; Reza Green, Esq.; Richard W. Bosk, Esq.

(57) ABSTRACT

The invention relates to a concept for placing a subcutaneous device such as a sensor at a selected site within the body of a patient, e.g. to obtain blood glucose readings. In a first aspect, an insertion needle comprises an oblong needle body and a distal end portion, the distal end portion having a pointed distal tip allowing the needle to be introduced subcutaneously and a distally facing generally smooth surface, the body comprising along a portion thereof a longitudinal groove adapted to at least partially accommodate the subcutaneous device. In a second aspect, a combination of an insertion needle and a subcutaneous device form an oblong body portion and a distal end portion formed by either of the members or in combination by the two members, the distal end portion having a pointed distal tip and a distally facing generally smooth surface. By the above configuration, a concept is provided reducing the severity of the body response following transcutaneous placement of a device as well as reducing the pain associated with the insertion.

4 Claims, 8 Drawing Sheets

ATRAUMATIC INSERTION OF A SUBCUTANEOUS DEVICE

This application claims the benefit of provisional application No. 60/366,675, filed Mar. 22, 2002.

The present invention relates generally to the insertion of subcutaneous devices. More specifically, the invention relates to an insertion device for placing a subcutaneous device at a selected site within the body of a patient, a needle-formed subcutaneous device as well as combinations of such devices. Especially, the invention relates to insertion means for easy transcutaneous placement of a sensor of the type used, for example, to obtain blood glucose readings.

BACKGROUND OF THE INVENTION

In the treatment of patients it would often be desirable to monitor a given parameter indicating the actual state of the treatment, e.g. monitoring the concentration of a drug dispensed to the patient or a body substance influenced by the drug. A given monitor system for measuring the concentration of a given substance may be based on invasive or non-invasive measuring principles. An example of the latter would be a non-invasive glucose monitor arranged on the skin surface of a patient and using near-IR spectroscopy, however, the present invention is concerned with the introduction of a transcutaneous device such as a sensor element.

In recent years, a variety of electrochemical sensors have been developed for a range of applications, including medical applications for detecting and/or quantifying specific agents in a patient's blood. As one example, glucose sensors have been developed for use in obtaining an indication of blood glucose levels in a diabetic patient. Such readings can be especially useful in monitoring and/or adjusting a treatment regimen which typically includes regular administration of insulin to the patient. In this regard, blood glucose readings are particularly useful in conjunction with feedback controlled medication infusion devices, e.g. of the external type carried by the patient.

Glucose sensors (as well as the infusion devices) may be fully implanted or may comprise a subcutaneous sensor communicating with a component carried externally by the patient. In either case, the body responds to the implant as an insult and produces a specialized biochemical and cellular response which may lead to the development of a foreign body capsule around the implant and consequently may reduce the flux of glucose to the sensor. The percutaneous approach aims to acquire data during the first few days of this tissue response.

The monitoring method can be of three types: non-reactive, reversibly reactive or irreversibly reactive. The type of sensor which, thus far, has been found to function most effectively in vivo is the amperometric sensor relying on irreversible, transport-dependent reactive glucose assays. For a detailed review of the different types of glucose sensors reference is made to Adam Heller, Implanted electrochemical glucose sensors for the management of diabetes, Annu. Rev. Biomed. Eng. 1999, 01:153–175.

The sensor may be placed subcutaneously being connected to external equipment by wiring or the substance (fluid) to be analysed may be transported to an external sensor element, both arrangements requiring the placement of a subcutaneous component, the present invention addressing both arrangements. However, for simplicity the term "sensor" is used in the following for both types of sensor elements.

Turning to the sensor elements per se, relatively small and flexible electrochemical sensors have been developed for subcutaneous placement of sensor electrodes in direct contact with patient blood or other extra-cellular fluid (for example by MiniMed Inc., see U.S. Pat. No. 5,482,473), wherein such sensors can be used to obtain periodic or continuous readings over a period of time. In one form, flexible transcutaneous sensors are constructed in accordance with thin film mask techniques wherein an elongated sensor includes thin film conductive elements encased between flexible insulative layers of polyimide sheet or similar material. Such thin film sensors typically include exposed electrodes at a distal end for transcutaneous placement in direct contact with patient blood or other fluid, and exposed conductive contacts at an externally located proximal end for convenient electrical connection with a suitable monitor device.

Insertion devices for this type of sensors are described in, among others, U.S. Pat. Nos. 5,390,671, 5,391,950, 5,568,806 and 5,954,643.

More specifically, U.S. Pat. No. 5,954,643 discloses an insertion set comprising a mounting base defining an upwardly open channel for receiving and supporting a proximal end of a flexible thin film sensor, the sensor further including a distal segment with sensor electrodes thereon which protrudes from the mounting base for transcutaneous placement, wherein the sensor distal segment is slidably carried by a slotted insertion needle fitted through the assembled base. Placement of the insertion set against the patient's skin causes the insertion needle to pierce the skin to carry the sensor electrodes to the desired subcutaneous site, after which the insertion needle can be slidably withdrawn from the insertion set. The mounting base further includes a fitting and related snap latch members for mated slide-fit releasable coupling of conductive contact pads on a proximal end of the sensor to a cable connector for transmitting sensor signals to a suitable monitoring device.

A similar arrangement is known from U.S. Pat. No. 5,568,806 disclosing an insertion set comprising an insertion needle extending through a mounting base adapted for mounting onto the patient's skin. A flexible thin film sensor includes a proximal segment carried by the mounting base and adapted for electrical connection to a suitable monitor or the like, and a distal segment protruding from the mounting base with sensor electrodes thereon for transcutaneous placement. The distal segment of the sensor and a distal segment of the insertion needle are positioned within a flexible cannula which extends from the mounting base, whereby placement of the mounting base onto the patient's skin causes the insertion needle to pierce the skin for transcutaneous placement of the cannula with the sensor therein. The insertion needle can then be withdrawn from the cannula and the mounting base to leave the sensor distal segment at the selected insertion position, with the sensor electrodes being exposed to patient blood or other extra cellular fluid via a window formed in the cannula.

Although the above-described insertion sets provide reliable means for introducing a needle formed sensor (i.e. having an oblong, needle-like appearance but not necessarily comprising a pointed distal tip), a number of disadvantages still prevail.

As stated above, the percutaneous approach aims to acquire data during the first few days after insertion of the device, after which a new sensor is placed at a different place. Although such a short period of time will remove the problems of long-term encapsulating reactions, a tissue response will immediately begin after insertion, the body trying to isolate the implanted object by tissue remodelling.

This response may have a profound and varying effect on glucose transport, even over a short period of use, e.g. 3–4 days, this calling for recalibration of the implanted sensor.

Besides the technical aspects of recalibration, opinions differ about how often recalibration will be necessary to ensure reliable performance and what patients may be willing to accept. Based on current experience with subcutaneous sensors, it is believed that the needle-type sensors will have to be recalibrated to blood glucose values obtained from the traditional fingerstick method at least once a day and maybe more often. In addition, putting calibration in the hands of patients presents safety and quality issues.

Although the available needle-type sensors are relatively small, they are still much larger than the infusion needles normally used when administering, for example, insulin. A further problem is therefore the pain and discomfort associated with the introduction of a needle sensor, for example when using the above-described prior art devices.

SUMMARY OF THE INVENTION

Having regard to the above discussion of the prior art, an object of the present invention is to provide an improved concept for the transcutaneous placement of a sensor device, the concept reducing the severity of the body response thereby allowing for more accurate measurements and/or a reduced need for recalibration of the sensor during the period of use. A further object of the invention is to provide an insertion device, a subcutaneous device or a combination thereof which reduces the pain experienced during insertion of a subcutaneous device such as a sensor. The devices should be safe and reliable in use as well as easy to use, compact in size and inexpensive to manufacture.

The present invention is based on the realisation, that the body responses to two different types of "influences": a response due to the "physical" action when the sensor is introduced (e.g. damaging tissue components) and left (e.g. compressing the neighbouring tissue), and a response due to the "presence" of the sensor (e.g. the nature of the materials and surfaces introduced). Although the latter indeed is of great importance, it is basically a materials problem which will not be addressed further in this application.

In contrast, the physically-based response directly results form the introduction procedures and the specific design of the sensor and introduction means utilized. In accordance with the invention, a subcutaneous device is provided allowing for substantially atraumatic insertion, the subcutaneous device comprising no cutting edges but merely a pointed distal end allowing the device to "gently" widening the tissue as the device is introduced. Ideally, such a procedure would cause as little tissue damage and pain as experienced when needles are introduced during acupuncture. The subcutaneous device in accordance with the invention may be in the form of the subcutaneous device to be placed, an insertion device therefore, or a combination thereof.

In contrast, the insertion device known from U.S. Pat. No. 5,954,643 utilizes a modified, traditional-looking hollow hypodermic needle, the only disclosed difference being a distal longitudinal slot allowing the needle to be withdrawn from the sensor. As is well know, such a needle comprises a pointed tip with knife-like edges extending proximally therefrom, this arrangement allowing the needle to cut through tissue.

In U.S. Pat. No. 5,568,806 the insertion needle is arranged through a cannula, the needle being described as terminating in a sharpened tip, i.e. also this prior art document teaches to use a cutting insertion device. Further, the distal end of the cannula tube is arranged substantially perpendicular to the general orientation of the cannula body, thereby producing a relatively sharp circumferential edge. In addition, using a cannula-formed sensor results in a sensor having a relatively large outer diameter, this resulting in a more traumatic introduction (producing additional pain as well as body response) as well as an increased pressure on the surrounding tissue when the sensor is implanted (this again resulting in pain as well as invoking a stronger body response).

Although a primary object of the present invention is to provide a less traumatic insertion of a subcutaneous sensor device, it readily appears that the principles providing a less painful insertion will have relevance for the introduction of any subcutaneous device.

Therefore, in a first aspect, an insertion needle for inserting a subcutaneous device is provided, the insertion needle comprising an oblong needle body and a distal end portion, the distal end portion having a pointed distal tip allowing the needle to be introduced subcutaneously and a distally facing generally smooth surface (i.e. comprising no cutting edge portions), the body comprising along a portion thereof a longitudinal recess adapted to at least partially accommodate the subcutaneous device. Preferably the distal end portion is conical.

In a preferred embodiment the recess terminates in the vicinity of the distal end portion, the recess having a ramp formed distally, the ramp facing outwardly-proximally relative to the needle body, i.e. a sloping surface joining the "floor" of the recess and the outer surface of the needle. The recess may have a length corresponding to at least 25%, preferably at least 50% of the length of the needle body or it may extend to the proximal end of the insertion needle. Advantageously the recess is in the form of a groove.

In combination with a subcutaneous device, the subcutaneous portion thereof (i.e. the portion adapted to be arranged subcutaneously) may be fully embedded in the recess or groove, i.e. fully "hidden" behind the distal end portion when seen distally from, or the sensor device may protrude out of the recess or groove in which case the protruding distal end of the sensor device should be provided with a rounded smooth surface having no sharp edges.

In a further embodiment the insertion needle is based on the configuration of a traditional hollow hypodermic needle, the normally knife-like edges extending proximally from the pointed distal end being rounded. To avoid "punching" of the tissue, the distal opening should be closed, either with additional means forming part of the insertion needle, or by the distal end of the sensor device, the two elements in combination forming a smooth distal surface.

In a second aspect, a combination of two members, an insertion needle and a subcutaneous device, is provided, the combined members forming an oblong body portion and a distal end portion, the latter being formed either by the insertion needle, the subcutaneous device or in combination by the two members, the distal end portion having a pointed distal tip and a distally facing generally smooth surface, i.e. comprising no cutting edge portions. It is to be noted that in the context of the present invention, the term "insertion needle" may also be used to denote an insertion device which does not necessarily comprise a pointed distal tip, but merely has a general "needle-like" appearance.

Preferably the subcutaneous device is more flexible than the insertion needle. In a preferred embodiment the two members are arranged side-by-side corresponding to at least a distal portion of the body, the members in combination forming an outer surface of the body. Gripping means may be provided between the two members for securely holding the subcutaneous device in place during insertion, yet allowing easy withdrawal of the insertion needle. In a further embodiment the two members are arranged coaxially, the subcutaneous device being in the form of a cannula, the insertion needle forming a core member protruding distally therefrom. In preferred embodiments the subcutaneous device is a sensor device.

In a third aspect a subcutaneous device is provided comprising an oblong body portion and a distal end portion, the distal end portion having a pointed distal tip allowing the needle to be introduced subcutaneously and a distally facing generally smooth surface (i.e. comprising no cutting edge portions), the device comprising at least one sensor element.

In a further aspect, a transcutaneous sensor insertion set is provided, comprising a mounting base adapted for mounting onto a patient's skin, a flexible sensor device having a proximal end attached to the base and a distal portion protruding from said mounting base, an insertion needle extending from the mounting base and supporting the sensor distal portion for transcutaneously placing the sensor distal portion when said mounting base is placed against a patient's skin, said insertion needle being withdrawable from the sensor and the mounting base, wherein the insertion needle and the sensor device in combination forms an insertion body, the insertion body comprising a distal end portion having a pointed distal tip and a distally facing generally smooth surface comprising no cutting edge portions.

The distally facing surface may be formed entirely by the insertion needle, the sensor device or as a combination of the two members as described in detail above.

At the proximal end portion of the insertion needle a gripping means is provided adapted for grasping and handling by a user. To properly orient the insertion body during insertion, the insertion set preferably comprises means for proper angular and/or rotational orientation of the insertion body relative to the mounting base during insertion. For example, the gripping means and the mounting base may be provided with releasable cooperating means for fixing the insertion needle in at least one predefined angular and/or rotational orientation.

In preferred embodiments, the distal portion of the sensor device is provided with at least one sensor element thereon for subcutaneously placing. By "sensor element" is meant any element or structure capable of being influenced by a body substance or condition and producing a signal corresponding thereto, e.g. an electrode as described in the above citations. Preferably the sensor device is provided with contact pads in electrical communication with the sensor electrode(s), the mounting base being adapted for connection with a cable connector for conducting the electrical signals to a processing unit.

It should be emphasized that the term "insertion set" in the context of the present application includes any device configuration comprising the defined means; e.g. the mounting base may be formed integrally with an infusion device or components thereof, this providing an infusion device with an integrated sensor.

In a further aspect, a method for inserting a subcutaneous device is provided, comprising the steps of: providing a combination of an insertion needle and a subcutaneous device, the combined members forming an oblong body portion and a distal end portion formed by either the insertion needle, the subcutaneous device or in combination by the two members, the distal end portion having a pointed distal tip and a distally facing generally smooth surface comprising no cutting edge portions, introducing the combined members through a patient's skin to a desired subcutaneous placement site, withdrawing the insertion needle to thereby leave the subcutaneous device at the placement site.

In a preferred embodiment of the method, a transcutaneous sensor insertion set is provided, comprising a mounting base adapted for mounting onto a patient's skin, the subcutaneous device being a flexible sensor device having a proximal end attached to the base and a distal portion protruding from said mounting base, the insertion needle extending from the mounting base forming the oblong body portion and the distal end portion, the insertion needle being withdrawable from the sensor and the mounting base, the method comprising the further steps of placing the mounting base against the patient's skin as the combined members are introduced.

BRIEF DESCRIPTION OF THE DRAWINGS

In the following the invention will be further described with references to the drawings, wherein.

It should be noticed that the figures are for illustrating the principles of the invention only and are not necessarily drawn to scale.

DESCRIPTION OF THE PREFERRED EMBODIMENTS

It should be emphasized that in the following disclosure of the invention, features and details which are not considered necessary for understanding the principles of the present invention has been largely omitted, for example, the sensor device is shown merely schematically, the attachment to a mounting base or similar structure or the provision of sensor electrodes and electric contact means being omitted.

FIGS. 1A–1E shows an embodiment of the invention in accordance with a first aspect. More specifically an insertion needle 10 comprises an oblong needle body 11 having a proximal portion 12 and a distal end portion 13, the distal end portion having a generally conical shape providing a pointed distal tip 14 and a distally facing smooth surface 15, thereby comprising no structures which may serve to cut tissue when the insertion needle is introduced subcutaneously. As appears from FIG. 1D the conical end portion completely defines the distal surface, the needle body comprising no protruding portions or element.

The needle body defines a general axis for the insertion needle, a longitudinal groove 20 being formed in the needle body coaxially therewith. As appears from FIG. 1A, the groove terminates in the vicinity of the distal end portion (i.e. just proximally of the conical portion), the groove having a ramp 21 formed distally (see FIG. 1B), the ramp facing outwardly-proximally relative to the needle body. Between the groove and the outer surface of the needle body two opposed edges 22, 23 are formed which preferably are rounded (not shown in FIG. 1C) to avoid any cutting action when the insertion needle is moved relative to the tissue.

Figure 1A:
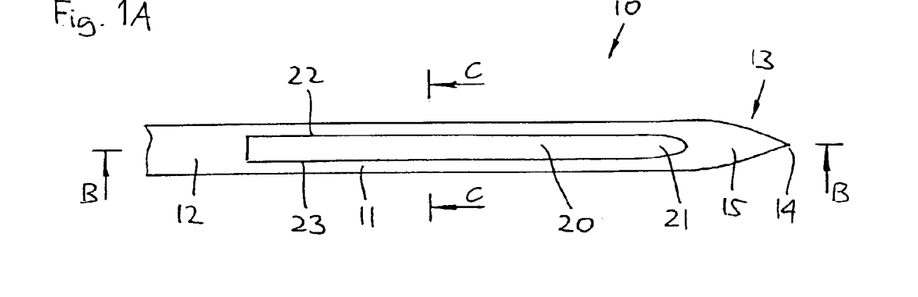
FIG. 1A shows a side view of an embodiment of the invention.
Figure 1B:
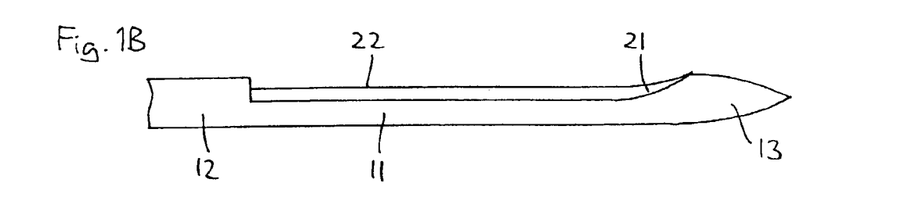
FIG. 1B shows a longitudinal cross-section of the embodiment shown in FIG. 1A.

The groove is adapted to at least partially accommodate a sensor device of which a distal end may slide on the ramp thereby forcing the sensor device outwardly relative to the insertion needle as will be described in greater detail below.

In the shown embodiment the groove terminates short of the distal and proximal end portions, however, it may extend along the full length of the needle body just at it may extend into the distal end portions, indeed, in which case the edge formed between the groove and the conical surface should be properly rounded to avoid any cutting action.

Figure 1C:
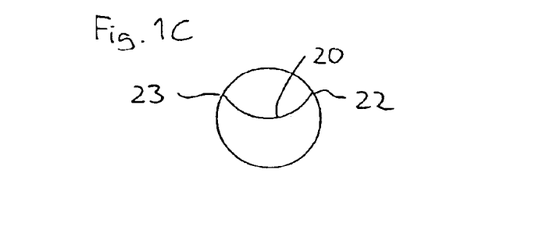
FIG. 1C shows a transverse section along the line C—C in FIG. 1A.
Figure 1D:
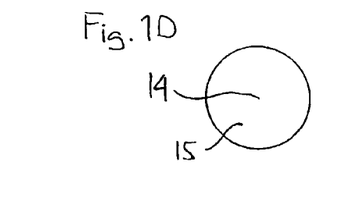
FIG. 1D shows a distal view of the embodiment shown in FIG. 1A.
Figure 1E:
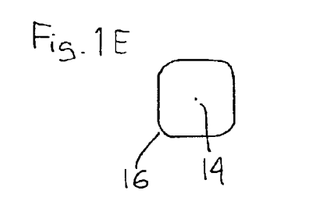
FIG. 1E shows a distal view of an alternative embodiment.

The shown insertion device has a general circular cross-section (not considering the groove) with a symmetrical "purely" conical end portion, however, the conical portion may be asymmetric, i.e. the pointed tip may be shifted towards a side, just as the cross-section may be non-circular, e.g. square with rounded edges 16 as illustrated in FIG. 1E. Indeed, the insertion needle may have varying cross-sections along the length thereof.

The insertion needle shown in FIGS. 1A–1C may be used with a sensor device which is partly or fully accommodated in the groove, i.e. the sensor device may be protruding or non-protruding in a cross-sectional view. In case the sensor device is fully accommodated in the groove, it may fully or partly "fill" the groove. An advantage with this arrangement is that the distal end of the sensor device is well protected against external forces during insertion, especially axial forces acting on the distally facing surface, which forces may act to displace or deform the sensor device. However, if deemed necessary, additional gripping means securing the sensor device during insertion may be provided as will be described in greater detail below.

Figure 2A:
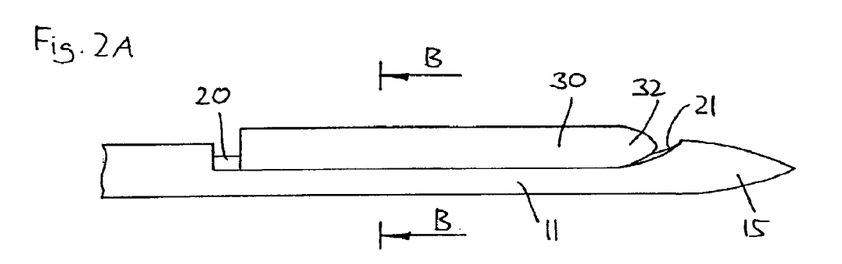
FIG. 2A shows a side view of a further embodiment of the invention.
Figure 2B:
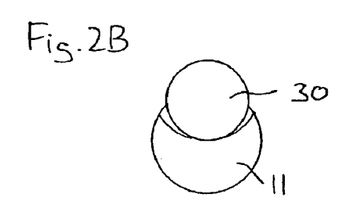
FIG. 2B shows a transverse section along the line B—B in FIG. 2A.
Figure 2C:
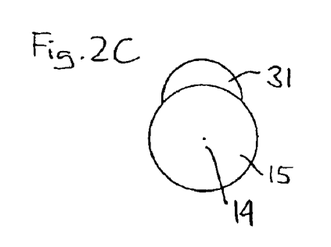
FIG. 2C shows a distal view of the embodiment shown in FIG. 2A.

As shown in FIGS. 2A–2C, a combination of an insertion needle 10 as described above and a sensor device 30 is provided, the sensor device being arranged in the groove 20 and is partly accommodated therein. As appears from FIGS. 2A–2C the sensor protrudes from the "virtual" circumference of the cylindrical needle body and thus beyond the conical distal surface of the insertion body as seen in FIG. 2C. However, in order to provide a smooth "combined" distal surface, i.e. made up of the distal surface of the introduction needle and the distally facing surface 31 of the protruding portion of the sensor device as seen in FIG. 2C, the latter is formed with a rounded distal end 32. As described above, axial forces acting on a protruding distally facing surface 31 may act to displace or deform the sensor device. Correspondingly, the sensor device and the insertion needle may be provided with releasable cooperating gripping means securing the sensor device during insertion, yet allowing easy withdrawal of the insertion needle.

Figure 3A:
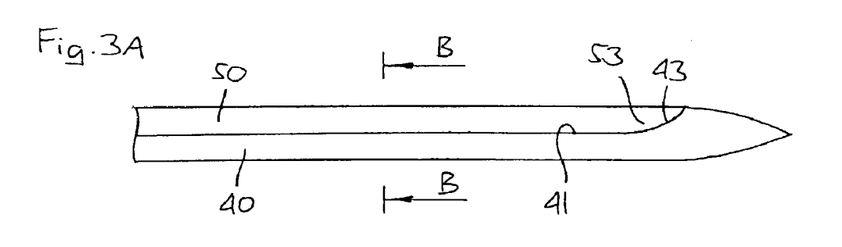
FIG. 3A shows a side view of a further embodiment of the invention.
Figure 3B:
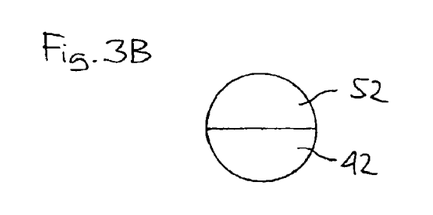
FIG. 3B shows a transverse section along the line B—B in FIG. 3A.

With reference to FIGS. 1 and 2, an insertion needle being provided with a recess in the form of a groove was described, however, the recessed area may have any desirable configuration serving the object of "nesting" the subcutaneous device to be inserted. FIGS. 3A and 3B show a combination of an insertion needle 40 and a sensor device 50, the needle comprising a recessed portion 41 accommodating the sensor, each component having a semicircular cross-sectional configuration 42, 52 thereby combining to form a circular body portion. As for the above-described embodiment, the recess terminates in a ramp 43, however, in contrast to above, the distal end 53 of the sensor is adapted to fully engage the ramp surface.

Next reference is made to FIGS. 4–8 disclosing combinations of an insertion needle (in the following also termed needle) and a sensor device, the combined device having a distal end portion with a pointed distal tip and a distally facing generally smooth surface comprising no cutting edges.

Figure 4A:
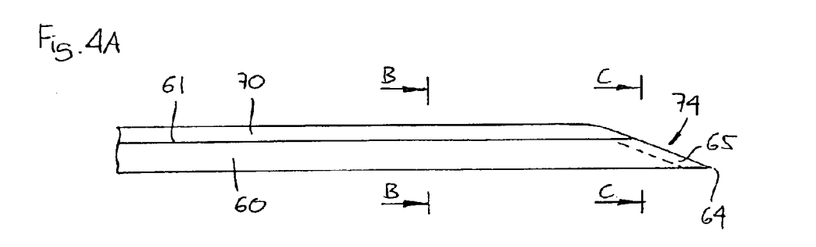
FIG. 4A shows a side view of a further embodiment of the invention.

FIG. 4A shows the distal portions of a slotted insertion needle 60 and a therein-mounted sensor device 70, the slot extending from the distal end and fully or partly to a proximal end, thereby forming a longitudinally extending groove 61. The slotted (part of the) needle has a part-circular cross sectional shape with an arcuate dimension or span greater than 180 degrees, e.g. a span of about 210 degrees which leaves a longitudinal slot in the needle with an arcuate dimension of about 150 degrees, which cooperates with the part-circular shape of the sensor device to define a substantially full-circle geometry for facilitated insertion through the patient's skin, see FIG. 4B. More specifically, the sensor device comprises a core 71 and two lateral flanges 72, 73, the core being gripped by the insertion needle and are thereby slidingly accommodated therein. The needle and sensor device are thus mechanically interlocked to prevent lateral dislocation of the latter from the insertion needle, while permitting longitudinal sliding motion of the needle over the sensor device.

The distal or free ends of the needle and the sensor device are set at an oblique angle to thereby form a common, smooth distal surface 74 providing a pointed distal end 64, the edges between the distal surface and the general circumference being properly rounded to prevent any cutting action when introduced subcutaneously, the rounded portion providing a needle distal surface 65. The shown rounding of the edges in the vicinity of the pointed end ensures that the pointed end is formed by the needle, the needle preferably being made form medical grade stainless steel, which allows the sensor to be formed from a relatively soft polymer less suitable for forming the pointed end.

In the shown embodiment the needle edge is rounded with a radius of curvature corresponding approximately to the wall thickness of the needle, which may be 0.2 mm for a needle having an outer diameter of 0.7 mm, however, a non-cutting radius of curvature may be less than 0.1 mm or even less than 0.02 mm.

Figure 4B:
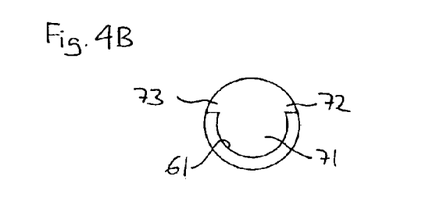
FIGS. 4B and 4C show transverse sections along lines B—B respectively C—C in FIG. 4A.
Figure 4C:
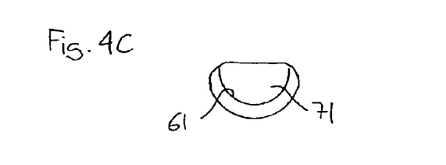
Figure 4D:
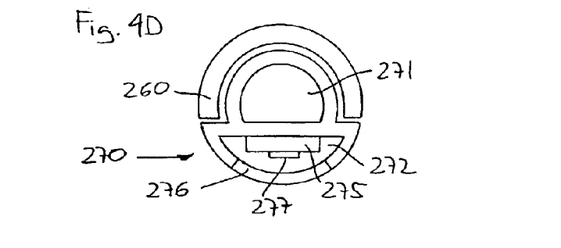
FIG. 4D shows a transverse sectional view of a specific sensor device configuration.

As appears, the sensor devices depicted in the different figures are shown "in solid" as they merely serve to illustrate the outer physical configuration thereof. With reference to FIG. 4D an example of a sensor arrangement mounted in an insertion needle 260 is shown, the sensor device being in the form of a cannula 270 comprising first and second lumen portions 271, 272, the first providing structural strength and having a part circular cross section to be fitted within the insertion needle, the second being adapted for receiving, protecting and guidably supporting a portion of the sensor element 275 per se. A window 276 is formed in the second lumen near the distal end thereof, in general alignment with the sensor electrodes 277 of the sensor element, to permit direct electrode exposure to patient body fluid when the sensor is transcutaneously placed. The cannula may be constructed from any suitable medical grade plastic or elastomer, such as polytetrafluoroethylene or silicone.

Figure 5A:
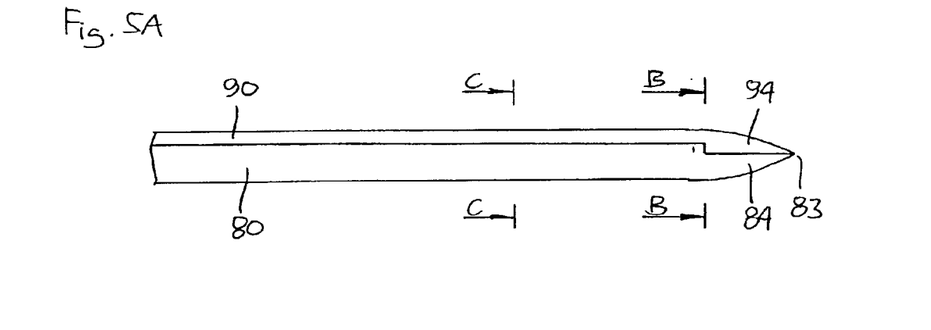
FIG. 5A shows a side view of a further embodiment of the invention.
Figure 5B:
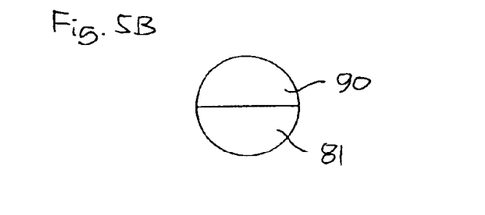
FIGS. 5B and 5C show transverse sections along lines B—B respectively C—C in FIG. 5A.
Figure 5C:
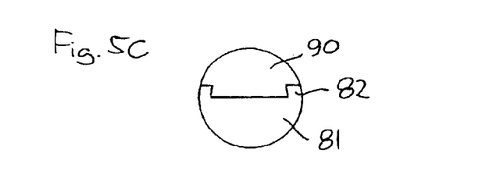

FIG. 5A shows the distal portions of a slotted insertion needle 80 and a therein-mounted sensor device 90. The slotted needle has a part-circular cross sectional shape with an arcuate dimension greater than 180 degrees which cooperates with the part-circular shape of the sensor device to provide a grip between the two members, see FIG. 5C, this essentially corresponding to the configuration of the above-described embodiment (FIG. 4B). However, in contrast to the previous embodiment, the needle is mainly solid, the solid portion 81 having a semicircular configuration with flange members 82 providing the gripping means. The two members form in combination a distal end portion having a pointed distal tip 83 and a distally facing smooth conical surface formed in combination by the distal surfaces 84, 94 of the two members. As was also the case above, the pointed end is provided by the needle, which necessitates the "solid" configuration of the needle. Indeed, in case the pointed tip is shifted away from the groove, a needle with a less solid cross-sectional configuration could be used. In case the tip was shifted entirely downwardly (in the figures), an overall configuration resembling the embodiment of FIG. 4A would result.

With reference to FIGS. 1–5, embodiments in which the pointed distal tip have been provided by a needle are described, however, by using a suitable (polymer) material for the sensor device, the pointed distal tip may be formed integrally therewith, this allowing for a simpler configuration of the needle (which then correctly may be denoted merely an insertion device)—or the insertion device may be entirely dispensed with.

Figure 6A:
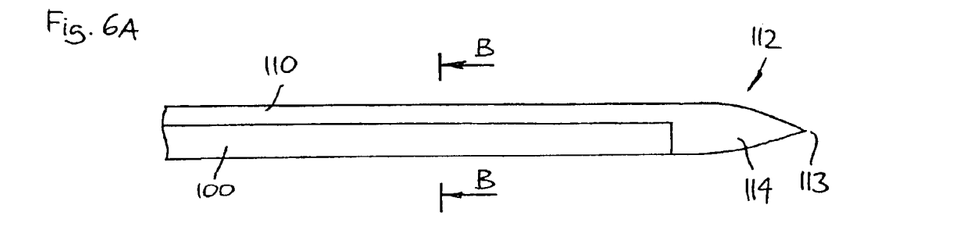
FIG. 6A shows a side view of a further embodiment of the invention.
Figure 6B:
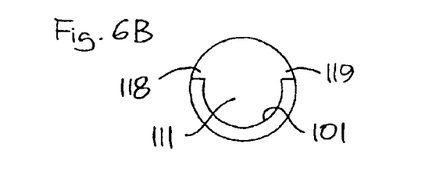
FIG. 6B shows a transverse section along the line B—B in FIG. 6A.

Correspondingly, FIG. 6A shows the distal ends of a slotted insertion device 100 and a therein-mounted sensor device 110, the slot extending from the distal end and fully or partly to a proximal end, thereby forming a longitudinally extending groove 101. The slotted (part of the) insertion device has a part-circular cross sectional shape with an arcuate dimension or span greater than 180 degrees, e.g. a span of about 210 degrees which leaves a longitudinal slot in the insertion device with an arcuate dimension of about 150 degrees, which cooperates with the part-circular shape of the sensor device to define a substantially full-circle geometry for facilitated insertion through the patient's skin, see FIG. 6B. More specifically, the sensor device comprises a core 111 and two lateral flanges 118, 119, the core being gripped by the insertion device and slidingly accommodated therein. The insertion device and sensor device are thus mechanically interlocked to prevent lateral dislocation of the latter from the insertion device, while permitting longitudinal sliding motion of the needle over the sensor device.

The distal end portion 112 having a pointed distal tip 113 and a distally facing smooth conical surface is formed entirely by the distal surface 114 of the sensor device 110, the insertion device solely serving as a support member providing a desired amount of stiffness.

Figure 7:
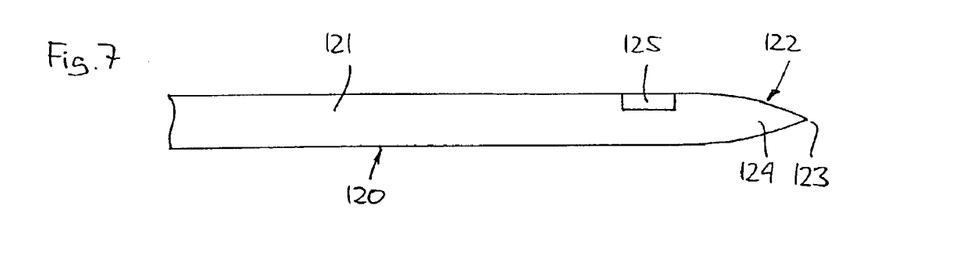
FIG. 7 shows a side view of a further embodiment of the invention.

In an even simpler embodiment of the present invention, the introduction device is fully dispensed with. More specifically, FIG. 7 shows a distal portion of a sensor comprising a distal body portion 121 and a distal end portion 122 having a pointed distal tip 123 and a distally facing smooth conical surface 124 formed entirely by the sensor device. The schematically shown sensor element 125 may represent a sensor element per se or a window covering such an element, this as described above.

Indeed, for a sensor device adapted to be introduced without a supporting insertion needle, a suitable balance between a desirable high rigidity during insertion and a high degree of flexibility when carried subcutaneously by a patient should be found, however, by using appropriate additional insertion means, it would be possible to insert even a relatively flexible sensor device. More specifically, insertion devices are known into which subcutaneous devices can be mounted, the insertion device comprising a user-releasable means for "driving" the device subcutaneously, e.g. by releasing a spring, this allowing a pointed but relatively flexible sensor device to be introduced.

The sensor device shown in FIG. 7 may also comprise an internal channel allowing a rigid support to be mounted therein during insertion.

Figure 8A:
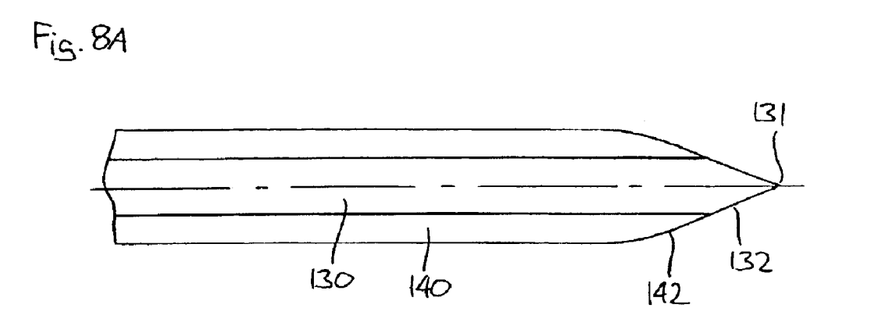
FIG. 8A shows a longitudinal cross-section of a further embodiment.
Figure 8B:
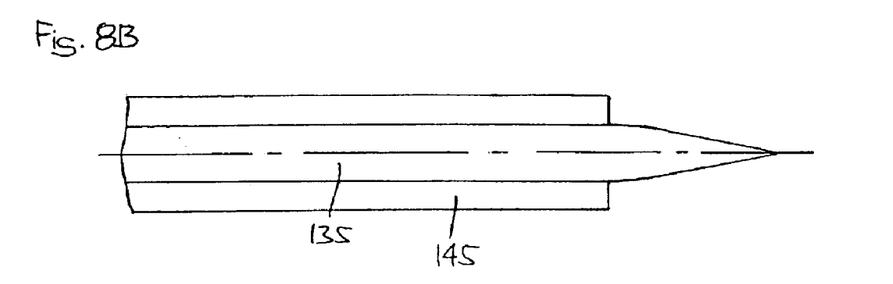
FIG. 8B shows a longitudinal cross-section of a prior art insertion needle and cannula.

In the above, insertion needles and sensor devices have described which are adapted to be arranged in a side-by-side configuration. In contrast, FIG. 8A shows the distal ends of a solid insertion needle 130 mounted through a sensor device 140 formed as a cannula. The two members form in combination a distal end portion having a pointed distal tip 131 and a distally facing smooth conical surface formed in combination by the distal surfaces 132, 142 of the two members. FIG. 8B shows an example of a prior art cannula 135 in combination with an "atraumatic" insertion needle 145. As appears, the two members do not form a common rounded surface and thus fail to provide for substantially atraumatic insertion.

Next, with reference to FIG. 9, a transcutaneous sensor insertion set 300 designed to place a sensor subcutaneously or at another selected site within the body of a patient, in a manner minimizing patient discomfort and trauma will be described. The flexible electrochemical sensor device 310 having a distal (or subcutaneous) portion 311 and a proximal portion 312 may be constructed according to so-called thin film mask techniques to include elongated thin film conductors embedded or encased between layers of a selected insulating material. The sensor electrodes 315 at the distal end portion are exposed through one of the insulating layers for direct contact with a patient body fluid (e.g. blood), when the distal portion of the sensor device is transcutaneously placed. By the term "flexible" in this context is meant that the sensor device along the length thereof is more flexible than the insertion needle.

The sensor 310 is carried by a mounting base 320 adapted for placement onto the skin of a patient. The mounting base comprises a generally rectangular pad having an upper surface 322 and an underside surface coated with a suitable pressure sensitive adhesive layer 321, with a peel-off paper strip (not shown) normally provided to cover and protect the adhesive layer, until the insertion set 300 is ready for use. The base further comprises an opening 325 through which the sensor device is arranged, the distal portion 311 protruding from the underside surface, the proximal portion 312 being carried by the upper surface. The proximal portion terminates in suitable conductive contact means 316 adapted for electrical connection to suitable signal processing means (not shown) for monitoring patient condition in response to signals derived from the sensor electrodes.

The insertion needle 330 is adapted for reception through a needle port 331 formed in the upper base and further through the opening 325. As appears, the insertion needle is of the same general configuration as shown in FIG. 1A, having a conically formed distal end portion 132 with a pointed tip 333 and an open groove 334 which extends longitudinally from just proximally of the tip at the underside of the needle to a position at least within the opening, the groove comprising a ramp formed distal portion 336. For the shown needle configuration, the opening 325 and the port 331 are "oversized" compared to the cross-section of the combined insertion needle and sensor distal portion, this allowing the wider distal portion of the insertion needle to be withdrawn. However, for other embodiments (e.g. corresponding to FIGS. 3–8) the needle may be received in slide-fit engagement through the opening and the port. Above the mounting base 320, the insertion needle may have a full round cross sectional shape, the rear end being anchored to an enlarged hub 335 adapted for easy grasping and handling between the thumb and index finger. Preferably the hub comprises guiding or locking means (not shown) for matingly engaging corresponding alignment or locking means on the mounting base.

In use, the insertion set 300 allows for quick and easy transcutaneous placement of the sensor distal portion 111 at a selected site within the body of a patient. More specifically, the peel-off strip is removed from the mounting base, at which time the mounting base 320 can be pressed onto and seated upon the patient's skin. During this step, the insertion needle 130 pierces the patient's skin and carries the needle-formed distal portion to the appropriate transcutaneous placement site. During insertion, the needle provides a stable support and guide structure to carry the flexible sensor device to the desired insertion site.

When the sensor device is transcutaneously placed, with the mounting base seated upon the patient's skin, the insertion needle 330 can be slidably withdrawn from the patient. During this withdrawal step, the insertion needle slides over the sensor device (to be described below) leaving the distal portion of the sensor with electrodes 115 thereon at the selected insertion site. These electrodes are directly exposed to patient body fluid (for example via a window as shown in FIG. 4D). The sensor proximal portion is appropriately coupled to processing means (not shown), so that the sensor can then be used over a given period of time for taking blood chemistry readings, such as blood glucose readings in a diabetic patient. If desired, the distal portion may comprise a lumen (as shown in FIG. 4D) available to deliver medication and/or sensor calibration fluid to the vicinity of the electrodes, or alternately to withdraw patient fluid such as blood for analysis.

Figure 9:
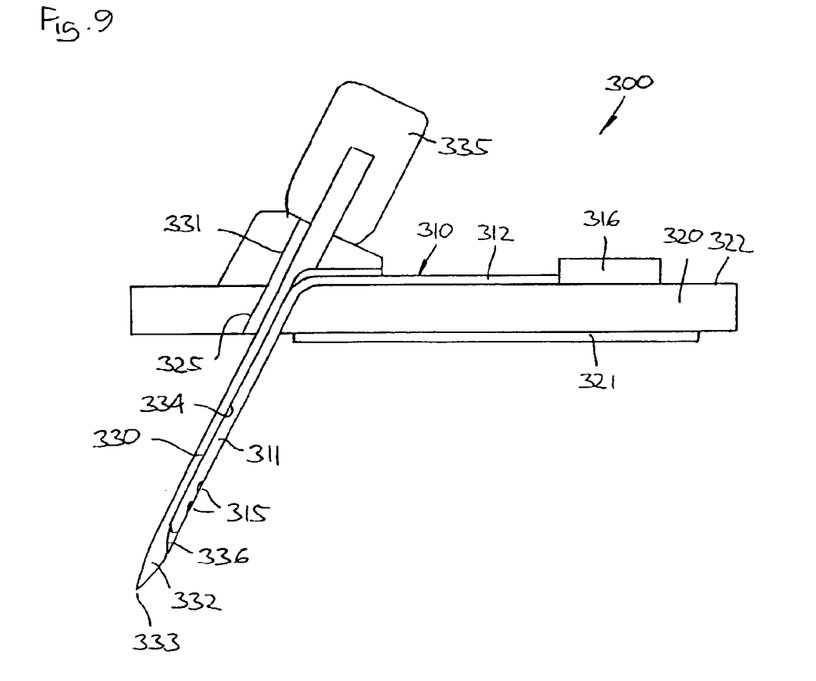
FIG. 9 shows a partial transverse section of an insertion set.
Figure 10A:
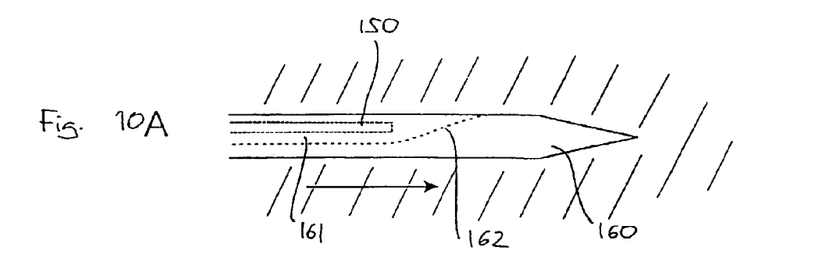
FIGS. 10A–10E show situations of use for an embodiment of the invention.
Figure 10B:
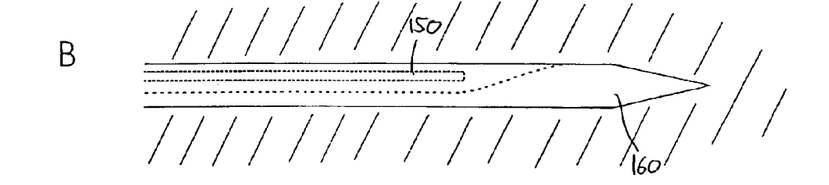
Figure 10C:
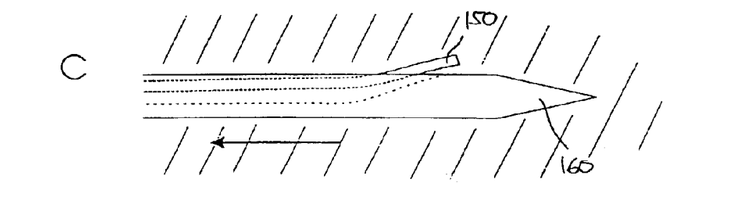
Figure 10D:
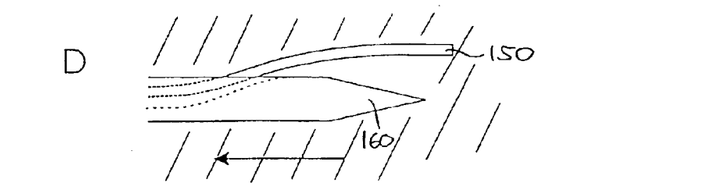
Figure 10E:
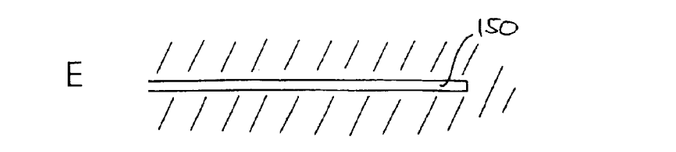

In case the configuration of the insertion needle and the sensor device correspond to the embodiments shown in FIGS. 3–8 the needle can be withdrawn from the sensor device without moving the latter, however, for the embodiments shown in FIGS. 1, 2 and 9, the sensor device 150 will be forced laterally out of the groove 161 as the needle 160 is withdrawn, this as illustrated in FIGS. 10A–10E. In a first step the combined device is introduced subcutaneously (FIGS. 10A and 10B). Next the sensor is held in place by the user (e.g. by the mounting base attached to the skin) and the needle is withdrawn (e.g. by gripping the hub), whereby the distal ramp-formed portion 162 of the groove will force the sensor device laterally (FIGS. 10C and 10D) allowing the distal end portion of the needle to slide along the sensor. When the needle has been retracted, the tissue will close around the sensor corresponding, to the channel formed by the needle during insertion (FIG. 10E).

In the above description of the preferred embodiments, the different structures have been described to a degree to which the concept of the present invention will be apparent to the skilled reader. The detailed construction and specification for the different components are considered the object of a normal design procedure performed by the skilled person along the lines set out in the present specification and the references cited.

While the present invention has been described in connection with the preferred embodiments shown in the various figures, it is to be understood that other similar embodiments may be used or modifications and additions may be made to the described embodiment for performing the same function of the present invention without deviating there from.

Therefore, the present invention should not be limited to any single embodiment, but rather construed in accordance with the appended claims.

What is claimed is:

1. A method for inserting a subcutaneous device, comprising the steps of:
   providing an assembly of an insertion needle and a subcutaneous device, the insertion needle comprising a pointed distal tip and a recess with an outwardly and proximally facing ramp, a distal portion of the subcutaneous device being arranged in the recess,
   inserting the insertion needle and the subcutaneous device subcutaneously,
   withdrawing the insertion needle relative to the subcutaneous device, the ramp thereby displacing the subcutaneous device laterally.

2. An assembly comprising an insertion needle in combination with a displaceable sensor device comprising at least one sensor element, the insertion needle comprising:
   a distal end portion having a pointed distal tip and a distally facing generally smooth surface,
   a needle body comprising along a portion thereof, a longitudinal recess terminating in the vicinity of the distal end portion and having a distal ramp facing outwardly and proximally relative to the needle body,
   the recess being adapted to at least partially accommodate the sensor device,
   wherein the sensor device is displaced laterally by the ramp when the insertion needle is moved proximally relative to the subcutaneous device.

3. An assembly comprising an insertion needle in combination with a displaceable flexible sensor device, the insertion needle comprising:

a distal end portion having a pointed distal tip and a distally facing generally smooth surface, a needle body comprising along a portion thereof, a longitudinal recess terminating in the vicinity of the distal end portion and having a distal ramp facing outwardly and proximally relative to the needle body, the recess being adapted to at least partially accommodate the flexible sensor device, wherein the flexible sensor device is displaced laterally by the ramp when the insertion needle is moved proximally relative to the subcutaneous device.

4. A transcutaneous sensor insertion set, comprising:

a mounting base adapted for mounting onto a patient's skin, a flexible sensor device having a proximal portion carried by the base and a distal portion protruding from the mounting base, the distal portion comprising at least one sensor element, an insertion needle comprising a distal end portion having a pointed distal tip and a distally facing generally smooth surface, and a needle body comprising along a portion thereof, a longitudinal recess terminating in the vicinity of the distal end portion and having a distal ramp facing outwardly and proximally relative to the needle body, the insertion needle extending from the mounting base and supporting the distal sensor portion for transcutaneously placing the distal sensor portion when the mounting base is placed against a patient's skin, wherein the insertion needle and the distal sensor portion in combination form an insertion body, the insertion needle being arranged for sliding withdrawal from the sensor device and the mounting base, and wherein the distal sensor portion is displaced laterally by the ramp when the insertion needle is withdrawn.

* * * * *